United States Patent
Wienand et al.

(10) Patent No.: US 9,068,913 B2
(45) Date of Patent: Jun. 30, 2015

(54) PHOTOLITHOGRAPHIC STRUCTURED THICK LAYER SENSOR

(75) Inventors: Karlheinz Wienand, Aschaffenburg (DE); Tim Asmus, Allendorf-Winnen (DE); Angela Maier, Aschaffenburg (DE); Karlheinz Ullrich, Gross-Umstadt (DE)

(73) Assignee: Heraeus Sensor Technology GmbH, Hanau (DE)

(*) Notice: Subject to any disclaimer, the term of this patent is extended or adjusted under 35 U.S.C. 154(b) by 110 days.

(21) Appl. No.: 13/319,767

(22) PCT Filed: May 6, 2010

(86) PCT No.: PCT/EP2010/002791
§ 371 (c)(1),
(2), (4) Date: Nov. 10, 2011

(87) PCT Pub. No.: WO2010/130370
PCT Pub. Date: Nov. 18, 2010

(65) Prior Publication Data
US 2012/0062254 A1  Mar. 15, 2012

(30) Foreign Application Priority Data
May 11, 2009  (DE) .................. 10 2009 020 743

(51) Int. Cl.
*G01N 15/00* (2006.01)
*G01N 15/06* (2006.01)

(52) U.S. Cl.
CPC ....... *G01N 15/0656* (2013.01); *Y10T 29/49002* (2015.01)

(58) Field of Classification Search
CPC .................. Y10T 29/49002; Y10T 29/49004; G01N 15/0656
USPC .................................. 324/658–691; 73/23.33
See application file for complete search history.

(56) References Cited

U.S. PATENT DOCUMENTS 6,437,551 B1 * 8/2002 Krulevitch et al. .......... 324/71.1
6,634,212 B2 * 10/2003 Moos et al. .................. 73/31.05
(Continued)

FOREIGN PATENT DOCUMENTS

DE  19845041 A1  4/2000
DE  10041921 A1  3/2002
(Continued)

OTHER PUBLICATIONS

Office Action issued Feb. 1, 2010 in DE Application No. 102009020743.0.
(Continued)

*Primary Examiner* — Jeff Natalini
(74) *Attorney, Agent, or Firm* — Panitch Schwarze Belisario & Nadel LLP

(57) ABSTRACT

A sensor, particularly an impedance sensor, for example a soot sensor, is provided which has two mutually electrically insulated electrodes, wherein at least one external electrode is formed from a composite of metal and inorganic oxide as a film pattern having a film thickness of 0.5 to 20 μm. The trace width of the film pattern and the spacing between the traces is 5 to 70 μm and the border region around the conductor trace edge varies less than 10 μm. Both electrodes can be arranged adjacent to each other as a film pattern in a plane. Preferably, the sensor has a heater. For mass production, electrodes are produced as a film pattern having a film thickness of 0.5 to 20 μm on electrically insulating oxide bases and, following full-surface imprinting of a metal powder and oxide-containing paste, the electrodes are structured particularly accurately as traces from the printed film. In particular, the film thickness of the printed film is reduced.

8 Claims, 2 Drawing Sheets

(56) References Cited

U.S. PATENT DOCUMENTS

| | | | |
|---|---|---|---|
| 6,972,685 B2* | 12/2005 | Sato et al. | 340/620 |
| 7,939,873 B2* | 5/2011 | Honda | 257/300 |
| 2003/0189433 A1* | 10/2003 | Lin et al. | 324/661 |
| 2005/0136598 A1* | 6/2005 | Bryant | 438/282 |
| 2006/0177349 A1* | 8/2006 | Thaysen et al. | 422/82.02 |
| 2008/0069490 A1* | 3/2008 | Abe et al. | 385/2 |
| 2009/0090622 A1* | 4/2009 | Ripley | 204/401 |
| 2009/0278556 A1* | 11/2009 | Man et al. | 324/693 |

FOREIGN PATENT DOCUMENTS

| | | |
|---|---|---|
| DE | 10308799 A1 | 9/2004 |
| DE | 102005029219 A1 | 12/2006 |
| DE | 102006043092 A1 | 3/2008 |
| DE | 102007021913 A1 | 11/2008 |
| EP | 1167955 A2 | 1/2002 |
| WO | 2007085838 A1 | 8/2007 |
| WO | 2008138849 A1 | 11/2008 |
| WO | 2009021734 A1 | 2/2009 |

OTHER PUBLICATIONS

Int'l Search Report issued Sep. 24, 2010 in Int'l Application No. PCT/EP2010/002791; Written Opinion.

* cited by examiner

PHOTOLITHOGRAPHIC STRUCTURED THICK LAYER SENSOR

CROSS-REFERENCE TO RELATED APPLICATIONS

This application is a Section 371 of International Application No. PCT/EP2010/002791, filed May 6, 2010, which was published in the German language on Nov. 18, 2010, under International Publication No. WO 2010/130370 A1 and the disclosure of which is incorporated herein by reference.

BACKGROUND OF THE INVENTION

The present invention relates to sensors, whose electrodes made of a composite material comprising oxide and platinum withstand an aggressive medium.

In screen printing technology, conductor traces 100 µm wide having a thickness of 10 to 100 µm are generated by the application of paste. Conductor traces that are 8 µm thick and 80 µm wide are also obtainable with this thick-film technology. However, with screen printing conductor traces having a thickness of less than 20 µm fray more at their borders, the thinner the application is. At 8 µm film thickness, the frayed border region has a width of about 30 µm. The finer structures of more complex thin-film or resinate technology are not resistant to aggressive media.

Impedance sensors, particularly based on an electrode comb structure, contain at least two mutually non-contacting platinum electrodes on ceramic substrates, for example on $Al_2O_3$ substrates. In contrast to heating resistors or measuring resistors, as for example temperature sensors, the two electrodes are each connected only to one potential of an electric power source, so that a voltage can be applied between the electrodes. A change of the dielectric between the electrodes is measured. The electrodes are brought into contact with the medium to be measured and are therefore arranged on an external side of a chip. If the electrodes, as for example soot sensors, are exposed to an aggressive medium, only electrodes produced by thick-film technology are suitable. However, such electrodes are inaccurate compared to less resistant sensors producible in thin-film or resinate technology.

BRIEF SUMMARY OF THE INVENTION

It is the object of the present invention to provide printed, highly sensitive sensors in mass production.

To achieve the object, finer electrode structures having a less frayed border region are produced.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there is shown in the drawings an embodiment which is presently preferred. It should be understood, however, that the invention is not limited to the precise arrangements and instrumentalities shown. In the drawings.

DETAILED DESCRIPTION OF THE INVENTION

Figure 1:
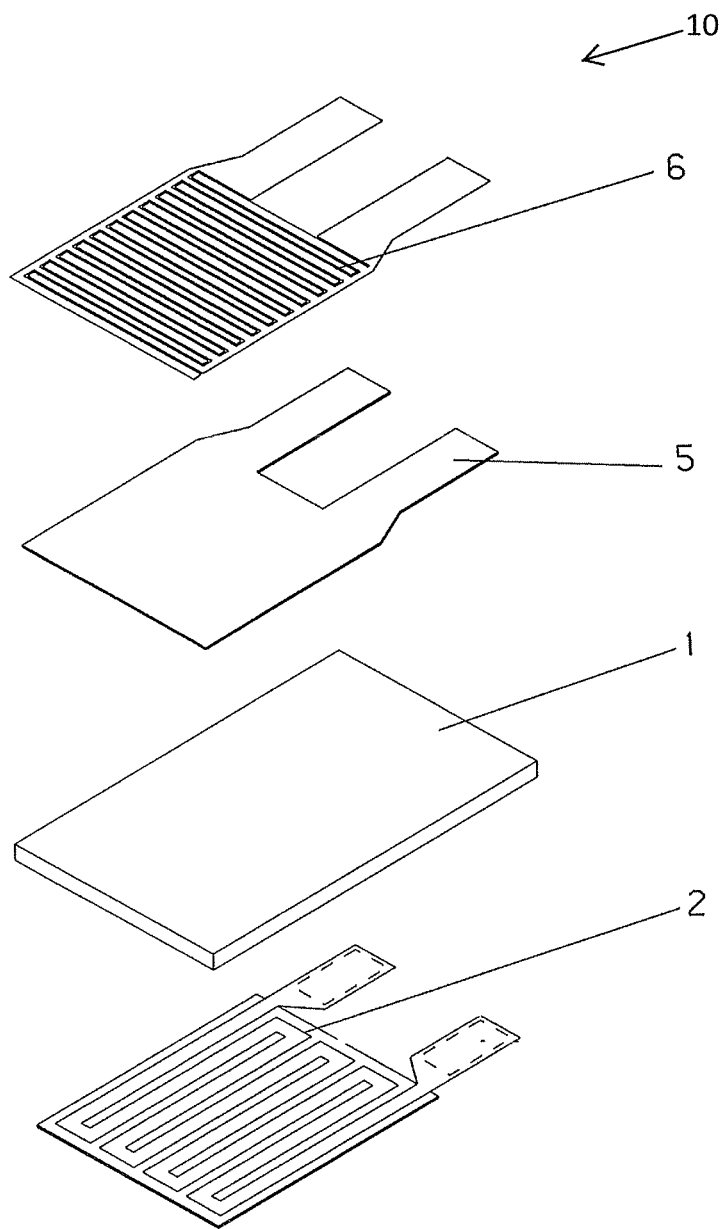
FIG. 1 is an exploded view of an impedance sensor according to a preferred embodiment of the present invention.
Figure 2:
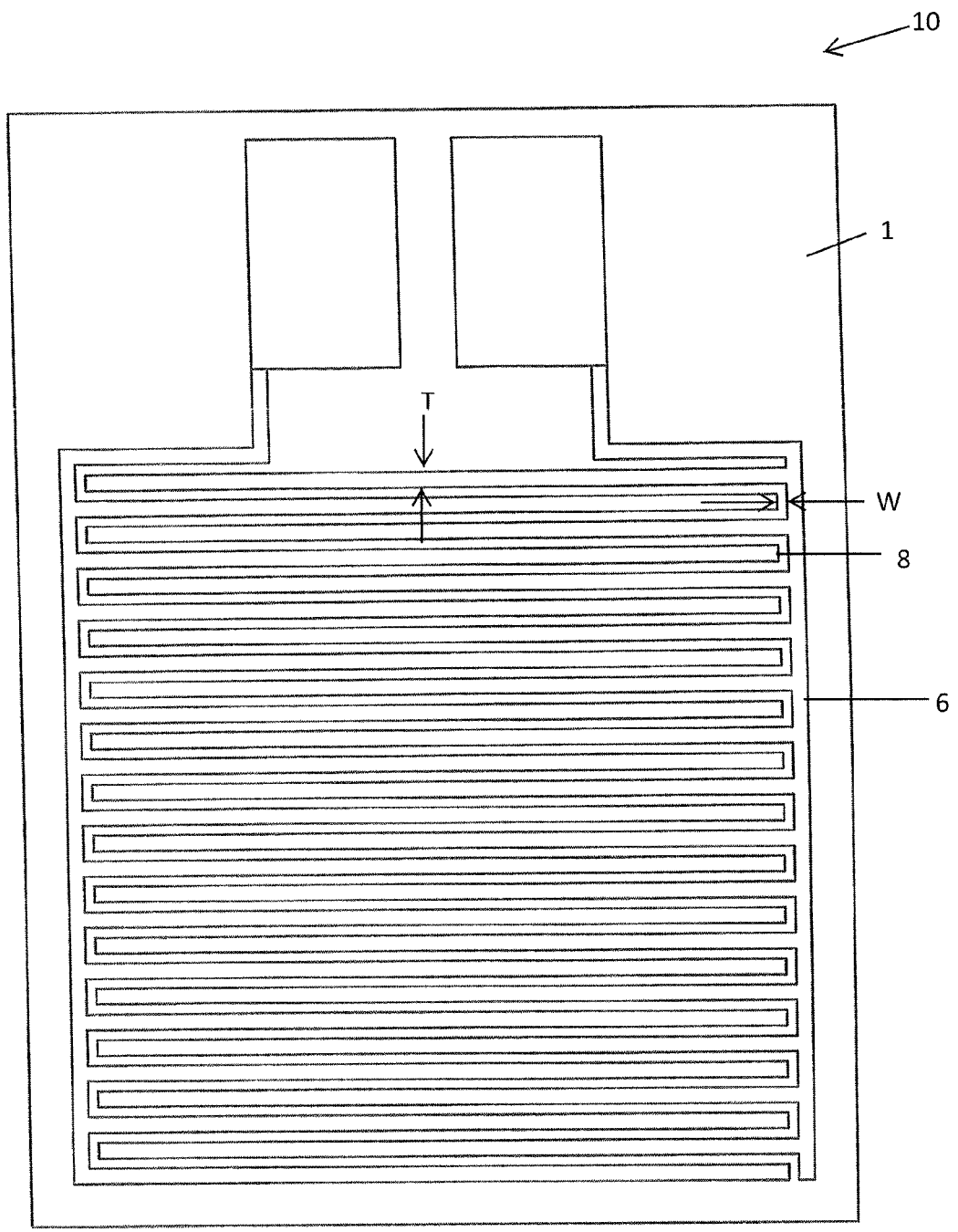
FIG. 2 is a top plan view of an impedance sensor according to a preferred embodiment of the present invention.

More particularly, referring to FIGS. 1-2, the object is achieved by a sensor, particularly an impedance sensor 10, comprising two mutually electrically insulated electrodes, wherein at least one external electrode 6 is formed of a composite of metal and inorganic oxide as a film pattern having a thickness T of 0.5 to 20 µm, characterized in that the trace width W of the film pattern and the spacing between the traces is 5 to 70 µm, wherein the border region 8 around the conductor trace edge varies less than 10 µm.

The object is further achieved by a process for mass production of sensors, wherein electrodes 6 are produced on electrically insulating oxide substrates 1 as a film pattern having a film thickness T of 0.5 to 20 µm, characterized in that, following full-surface imprinting of a metal powder and oxide-containing paste, the electrodes 6 are so accurately structured as traces from the printed films 5, that their widths W and spacings are set between 5 and 70 µm, and the border region 8 around the conductor trace edge varies less than 10 µm.

According to the invention, the trace width W is between 5 and 70 µm. Particularly, it is at least 20 µm or not more than 60 µm. Likewise, the spacing between the traces is between 5 and 70 µm, and preferably is at least 15 and not more than 60 µm.

The border region 8 around the conductor trace edge varies less than 10 µm, particularly 2 to 5 µm. According to the invention, these fine and accurate structures achieve a measurement accuracy, as previously attainable only with thin-film technology. Compared to thin-film technology, the cost of this is reduced.

The externally arranged electrode film structure is formed as a composite of metal, particularly based on the platinum group metals Pt, Ir or Pd, and inorganic oxide, particularly based on glass and optionally ceramic, having a film thickness T of 0.5 to 20 µm, particularly 1 to 4 µm. According to the invention, the resistance of the electrodes 6 to aggressive media corresponds to thick-film technology.

The metal, particularly precious metal, effects the electrical conductivity of the composite and must be resistant to aggressive media. It contains more than 50 wt. % of platinum group metal and optionally less than 50 wt. % of another precious metal, Au or Ag, for example as PtRh, IrPt or PdAg alloys. Due to the formation of the volatile and toxic tetroxide, Os is excluded from the preferred platinum group metals. The metals Ag and Au to be used at a total weight of less than 50 wt. % preferably comprise less than 30 wt. %.

The inorganic oxide of the composite effects substrate adhesion and a particularly high resistance to abrasive and aggressive media. Mixtures of glass, particularly based on $SiO_2$ and ceramic material, for example $Al_2O_3$ or MgO, have proven successful.

Preferably, the external film structure comprises two mutually electrically insulated electrodes 6. For this purpose, they are mounted on an electrically insulating base, particularly an electrically insulating substrate 1.

Alternatively, the two electrodes are insulated by an electrically insulating film, particularly a thin film of $Al_2O_3$. For example, an electrode structure comprising an electrode is covered with an electrically insulating thin film, and a single external electrode is produced on the electrically insulating thin film. Alternatively, the covered electrode can be produced in thin-film technology.

In particular, the sensor has a heating resistor 2. This allows a self-cleaning through free-firing of the sensor.

For producing the sensors 10, pastes comprising metal and inorganic oxide are initially applied with a paste film thickness T of 0.5 to 20 µm over the full surface on electrically insulating oxide bases, particularly ceramic substrates 1. Only after the full surface printing of the paste are traces structured from the printed films 5. In this way, the widths and spacings can be set between 5 and 70 μm, and the varying border region around the conductor trace edge can be kept below 10 μm.

The paste film 5 is fired onto the substrate 1. This removes the organic components of the paste. The glass component of the paste thereby binds the inorganic components of the paste to the substrate 1. Preferably, the paste contains ceramic material in addition to the inorganic glass and metal components, in order to enhance the resistance to abrasive materials and aggressive chemicals.

Preferably, the film thickness T of the printed film is reduced, for example by sputter etching. In structuring by means of etching, it has proven successful to carry out the reduction in film thickness before the structuring, because the structuring is less accurate with increasing film thickness. In laser-structuring, it has proven successful to reduce the film thickness only after structuring. Here, ridges formed in laser-structuring are again somewhat smoothed. In sputter etching, the film is used as the target.

Here, it has proven successful to apply a conductive paste at a thickness of more than 7 μm, and according to the invention, to reduce it to a film thickness T of less than 5 μm, particularly less than 4 μm.

For mass production, a plurality of electrode structures 6 is generated on a substrate, for example more than 100 on a 2×2-inch substrate, or more than 1,000 on a 4×4-inch substrate.

In this way, a plurality of sensors 10 is produced at the same time, which are separated after their co-production.

Preferably, a heating resistor 2 is integrated in the chip. Heating resistors 2 manufactured by screen printing can be printed on the back side of the substrate 1. Alternatively, heating resistors 2 are printed on a separate substrate and the substrate 1 of the electrodes 6 is attached to these heating resistors. As another alternative, the heating resistors are arranged in a layer adjacent to the electrodes, in which for example a conductor trace operable as a heating resistor is arranged adjacent to the full-surface paste application for the electrodes, or the conductor trace for the heating resistor takes place simultaneously with the structuring of the electrodes from the full-surface paste print.

Example

Mass Production

A paste comprising flux, glass ceramic and one of the metals Pt or PtRh10 or Ir or PdAg is thinly applied by screen printing on the full surface of a 2×2 or 4×4-inch substrate made of 96% $Al_2O_3$ and fired to a film having a thickness of 8 μm.

Thereafter, the entire surface is be etched to a film thickness of 3 μm by a sputter etching process, in which the fired film is polarized as a target (dry etching).

The 3 μm thick film is photolithographically structured with 2×2 inches to 300 or with 4×4 inches to 1,200 electrode comb pairs having a trace width of 50 μm and 30 μm spacing between the traces.

Then separation takes place into 300 and 1,200 chips, respectively, and mounting of one chip each onto carriers.

The chips are connected to suitable measuring devices for measurement of soot in exhaust systems of diesel engines It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

The invention claimed is:

1. A sensor comprising two mutually electrically insulated electrodes, at least one of the insulated electrodes being an external electrode comprising a composite of metal and inorganic oxide as a film pattern having a thickness of 1 to 4 μm, wherein the metal comprises platinum, iridium or palladium and the inorganic oxide comprises glass, wherein the external electrode is structured as traces from the film pattern, wherein a trace width of each of the traces is between 20 and 60 μm, wherein a spacing between traces is 15 to 60 μm, and wherein a border region around a trace edge of each of the traces varies between 2 and 5 μm.

2. The sensor according to claim 1, wherein the two electrodes are arranged adjacent to each other as a film pattern in one plane.

3. The sensor according to claim 1, further comprising a heating resistor.

4. The sensor according to claim 1, wherein the sensor is a soot sensor.

5. The sensor according to claim 4, wherein the inorganic oxide further comprises a ceramic.

6. The sensor according to claim 1, wherein the sensor is an impedance sensor.

7. A process for mass production of sensors, the process comprising producing electrodes on electrically insulating oxide substrates as a film pattern having a film thickness of 1 to 4 μm, wherein following full-surface imprinting of a metal powder and oxide-containing paste to produce printed films, the electrodes are so accurately structured as traces from the printed films that their widths are set between 20 and 60 μm, spacings between the traces are set between 15 and 60 μm, and a border region around a trace edge of each of the traces varies between 2 and 5 μm, and wherein the film pattern is formed of a composite of a metal comprising platinum, iridium or palladium and an inorganic oxide comprising glass.

8. The process according to claim 7, wherein the inorganic oxide further comprises a ceramic.

* * * * *